United States Patent [19]

Eek et al.

[11] Patent Number: 5,599,794
[45] Date of Patent: Feb. 4, 1997

[54] SYNERGISTIC COMBINATION OF A SUBSTANCE WITH GASTRIC ACID SECRETION INHIBITING EFFECT AND AN ACID DEGRADABLE ANTIBIOTIC

[75] Inventors: Arne T. Eek, Trosa; Sven Erik Sjöstrand, Södertälje, both of Sweden

[73] Assignee: Aktiebolaget Astra, Sodertalje, Sweden

[21] Appl. No.: 51,722

[22] Filed: Apr. 22, 1993

[30] Foreign Application Priority Data

Apr. 24, 1992 [SE] Sweden ................................ 9201297
Jan. 8, 1993 [SE] Sweden ................................ 9300029

[51] Int. Cl.⁶ ........................ A61K 31/70; A61K 31/445
[52] U.S. Cl. ............................................ 514/29; 514/327
[58] Field of Search ........................ 424/114; 514/327, 514/29

[56] References Cited

U.S. PATENT DOCUMENTS 5,013,743  5/1991  Iwahi et al. ............................ 514/338
5,093,342  3/1992  Tomoi et al. .......................... 514/328

FOREIGN PATENT DOCUMENTS

WO9009175  2/1990  WIPO.
WO9204898  4/1991  WIPO.

OTHER PUBLICATIONS

Logan et al, The Lancet, vol. 340, Jul. 25, 1992 Abstract
Drug Thev Boll 1991, 29; 26 reference (see foot note #9).
Chemical Abstracts 104:203737 j (1986).
Chemical Abstracts 106:182648l (1987).
P. Unge, et al. "Does Omeprazole, 40 mg o.m. improve antimicrobial therapy directed towards gastric Campylobacter–pylori in patients . . . " Scandinavian Journal of Gastroenterology 1989, 24 (Suppl. 166) p. 184 (ABSTRACT).

P. Unge, et al. "Does Omeprazole improve antimicrobial therapy directed towards gastric Campylobacter–pylori in patients with antral gastritis" Scandinavian Journal of Gastroenterology 1989, 24 (Suppl. 167) p. 49–54 (ARTICLE).
"Which regimen for H pylori eradication?" SCRIP No. 1861 Oct. 5, 1983, p. 23.
S. Rune, "Helicobacter pylori, Peptic Ulcer Disease and Inhibition of Gastric Acid Secretion" Digestion 1992; 51 (Suppl. 1): 11–16.
McDermott, et al., Science, The Absorption of Orally Administered Penicillin, Mar. 22, 1946, pp. 359–361.
McNulty, et al., Eur. J. Clin. Microbiol. Infect. Dis., Susceptibility of Clinical Isolates, Aug., 1988, pp. 566–569.
The Lancet, Clarithromycin and Omeprazole, vol. 340, Jul. 25, 1992.
Goodwin, Worsley, Peptic Ulcer Disease, 1992, Current Science, 8:122–127.
Loo, Sherman, Matlow; Helicobacter pylori Infection, Anti-–microbial Agents & Chemotherapy, May, 1992, pp. 1133–1135.

Primary Examiner—Jerome D. Goldberg
Attorney, Agent, or Firm—White & Case

[57] ABSTRACT

The invention consists of a combination of a substance that increases the intragastric pH and an acid degradable antibacterial compound. By this combined product regimen it will be possible to obtain maximal local antibacterial effect of acid degradable antibiotics as well as enhanced bioavailability of the active antibiotic, thus resulting in higher amounts of the active compound in the gastric mucosa due to secretion of weak bases. Both pharmacological effects contribute to drastically increased antimicrobial capacity of acid degradable antibiotics to be used against local infections in the gastrointestinal tract causing gastritis and/or peptic ulcer. The invention also selects to the use of said combination and a process for the preparation thereof.

2 Claims, 2 Drawing Sheets

SYNERGISTIC COMBINATION OF A SUBSTANCE WITH GASTRIC ACID SECRETION INHIBITING EFFECT AND AN ACID DEGRADABLE ANTIBIOTIC

FIELD OF THE INVENTION

The present invention relates to a combination of a substance with inhibiting effect on the gastric acid secretion, thus a substance which increases the intragastric pH e.g. proton pump inhibitors, histamin-$H_2$-blockers and one or more antibacterial compounds which are acid degradable.

BACKGROUND OF THE INVENTION

In the treatment of the peptic ulcer disease current therapy aims at reducing the gastric acid secretion, thus resulting in a recess of the injuries in the gastro-intestinal tract. Inhibitors of the gastric acid secretion, proton pump inhibitors in particular, induce a rapid relief of pain and other symptoms associated with the ulcer disease. However, relapses of the disease is a documented fact. Since gastric antisecretory therapy only leads to reduction of the major tissue irritating factor, gastric acid, the plausible cause of the disease, Helicobacter pylori, remains mainly unaffected. (Helicobacter pylori was earlier named Campylobacter pylori.)

Helicobacter pylori is affected by certain antibiotic compounds e.g. macrolides and penicillins as has been shown in vitro and in vivo. However, these products are degraded into nonantibacterial metabolites in the presence of gastric acid, which drastically reduces their antibacterial efficacy.

In view of the widespread use of antimicrobial pharmaceuticals in the treatment of infectious diseases or for other purposes and the consequent emergence of drug-resistant strains, increased incidence of microbial substitution due to disturbance of the normal bacterial flora, changes in profile of infectious diseases, etc., there has been a constant demand for the development of new antimicrobial agents or combinations thereof.

PRIOR ART

Proton inhibitors e.g. omeprazole and its pharmaceutically acceptable salts, which are used in accordance with the invention, are known compounds, e.g. from EP 5129 and EP 124495 and can be produced by known processes. From US 5093342 it is also known that omeprazole can be used in the treatment of Helicobacter infections. Further it has earlier been proposed in WO 92/04898 to use a specific antibiotic, amoxycillin, which is stable in gastric acid, in combination with pantoprazole in the treatment of duodenal ulcers. No specific test data are included in said document.

From e.g. Science, Mar. 22, 1946, p. 359–361 it is known that if acid degradable penicillins are administered orally they will be destroyed by the acid content in the stomach.

Further it is described in Eur. J. Clin. Microbiol. Infect. Dis, August 1988, p. 566–569 that some acid degradable antibiotics are active in vitro against Helicobacter pylori.

OUTLINE OF THE INVENTION

It has now unexpectedly been found that a combination of a substance with inhibiting effect on the gastric acid secretion, thus a substance which increases the intragastric pH e.g. proton pump inhibitors, histamin-$H_2$-blockers and one or more antibacterial compounds which is acid degradable give high plasma concentration of the antibiotic following oral administration.

By reducing the acidity in the stomach it is possible to markedly increase the bioavailability of acid-degradable antibiotics thus leaving more of a given dose of the compound available for local antibacterial effect as well as for absorption. Selection of narrow-spectrum antibiotics e.g. benzylpenicillin is favourable since such antibiotics have few side-effects. Due to known physico-chemical properties in general of weak bases like for instance omeprazole, the selection of weak bases e.g. erythromycin favours an increased accumulation of the antibiotic in the stomach wall and gastric crypts where the microbs e.g. Helicobacter pylori resides.

Thus, by combining the components of the present invention synergism of the antibacterial effect of antibiotic compounds is achieved resulting in an improved therapeutic efficacy.

DETAILED DESCRIPTION OF THE INVENTION

Figure 1:
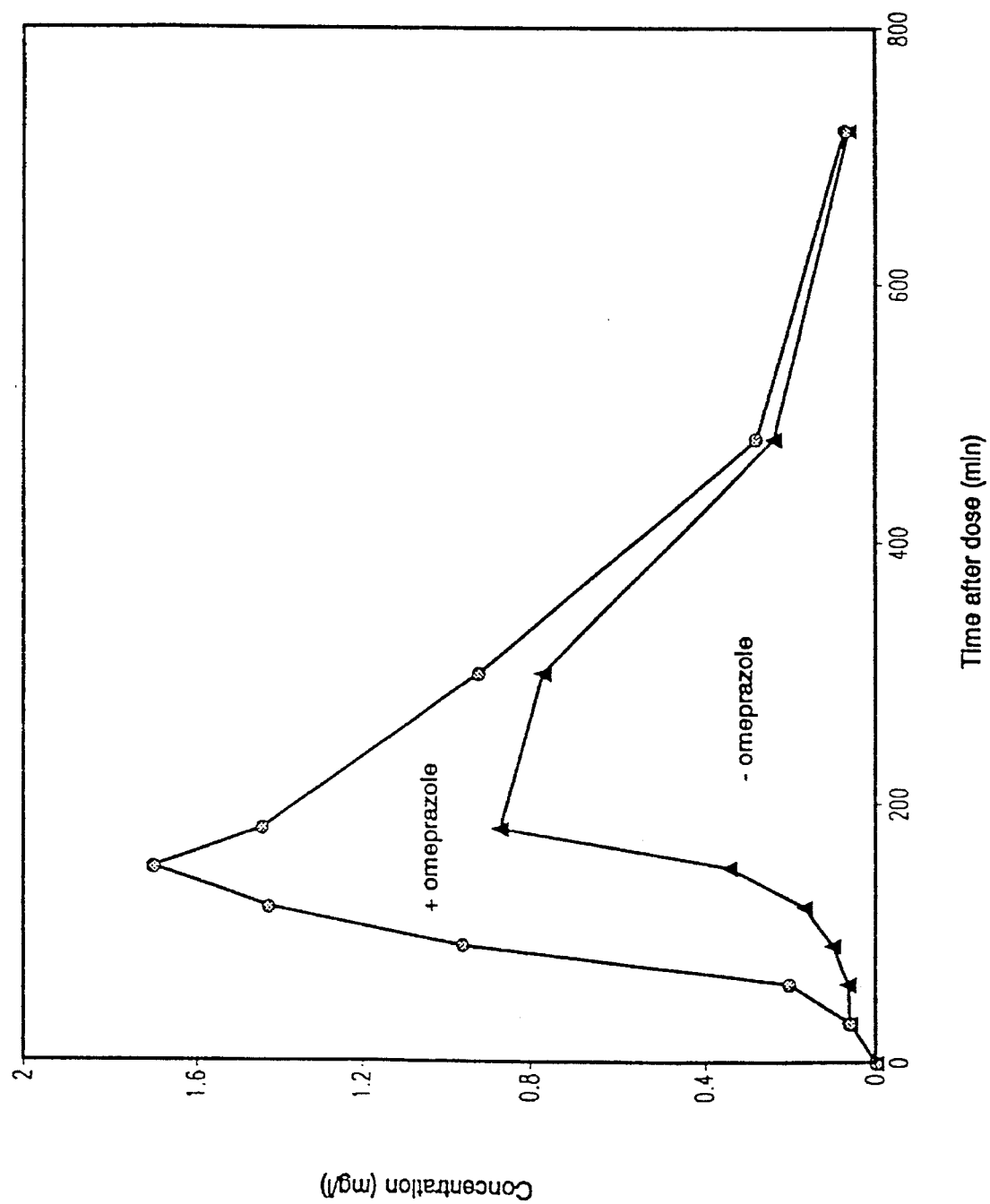
FIG. 1 represents a graph showing the blood serum levels of erythromycin Ery-Max® in healthy subjects during treatment with and without omeprazole.

The new combination is especially directed to the treatment of gastropathies e.g. induced by Helicobacter pylori infections. Helicobacter pylori is a gram-negative spirilliform bacterium which colonises in the gastric mucosa. Treatment with commonly used acid degradable antibiotics alone has given insufficient effect.

The combination of 5-methoxy-2-{[(4-methoxy-3,5-dimethyl- 2-pyridinyl)methyl]sulfinyl}-1H-benzimidazole (generic name: omeprazole) or pharmaceutically acceptable salts thereof and an acid degradable antibiotic give an especially high plasma concentration of the antibiotic following oral administration.

The salt of omeprazole according to the invention is an alkaline pharmaceutically acceptable salt. Examples of such salts include inorganic salts, such as alkali metal salts, e.g. sodium salt, potassium salt etc., alkaline earth metal salts, e.g. calcium salt, magnesium salt etc., ammonium salt, organic salts such as organic amine salts, e.g. trimethylamine salt, triethylamine salt, pyridine salt, procaine acid, picoline salt, dicyclohexylamine salt, N,N-dibenzylethylenediamine salt, N-methylglucamine salt, diethanolamine salt, triethanolamine salt, tris(hydroxymethytamino)methane salt, phenylethylbenzylamine salt, dibenzylethylenediamine salt.

Also other proton pump inhibitors, such as lansoprazole may be used according to the invention. The antibiotic used in the combination should be of the kind, which has a bioavailability which may be improved due to elevation of intragastric pH. It should also be an antimicrobial compound with a very narrow spectrum e.g. benzylpenicillin.

Other examples are acid degradable and acid semi-stable macrolides e.g. erythromycin base and clarithromycin (Nakagawa et al., Chem. Pharm. Bull., 1992, 40, 725–28). Further examples are antibiotics and/or salts thereof which are pharmaceutically engineered for acid protection like for instance enteric coating (e.g. Ery-Max®).

The antibacterial activity against Helicobacter pylori as indicated by MIC-values of macrolides is drastically decreased with increased pH of the medium in vitro (Melanoski et al., ICAAC, 1992, abstract 713, p 229).

The combination according to the present invention can be produced in one pharmaceutical formulation comprising both active ingredients or in two separate tablets or capsules, powder, mixture, effervescence tablets or solution.

The active ingredients according to the invention are administered in the form of a pharmaceutical preparation containing the active ingredients as such (e.g. the free base in the case of erythromycin) or in the case of omeprazole also as a salt thereof in combination with a pharmaceutically acceptable carrier by the oral or parenteral route. The carrier mentioned above may be a solid, semi-solid or liquid diluent or a capsule. Compatible dosage forms include various types of tablets, capsules, granules, powders, oral liquids, injections and so on. The proportions of the active ingredient in the total composition is generally 0.1 to 100 weight percent and preferably 0.1 to 95 weight percent.

In the manufacture of a pharmaceutical preparation for oral administration, the active ingredient can be formulated with a solid particulate carrier such as lactose, sucrose, sorbitol, mannitol, starch, amylopectin, a cellulose derivative or gelatin, and a lubricating agent such as magnesium stearate, calcium stearate or polyethylene glycol wax may be further incorporated. The resulting composition is then compressed into tablets. Coated tablets or dragees can be manufactured by coating the core tablets, thus prepared, with a thick sugar solution containing gum arabic, gelatin, talc, titanium dioxide, etc. or a lacquer prepared using a volatile organic solvent or solvent mixture.

Soft gelatin capsules can be manufactured by filling a composition comprising the active ingredient and a known vegetable oil into capsules. Hard gelatin capsules can be manufactured by filling into capsules the granules or pellets each comprising the active ingredient and a solid particulate carrier such as lactose, sucrose, sorbitol, mannitol, potato starch, corn starch, amylopectin, a cellulose derivative or gelatin.

The dosage of omeprazole or a salt thereof and the antibiotic depends on individual needs (for example, the patient's condition, body weight, age, sex, etc.) as well as on the method of administration. Generally speaking, the oral dosage may range from 1 to 200 mg of omeprazole per day and up to 10 g of acid degradable antibiotic per adult human. Each may be administered in one to a few divided doses.

PHARMACOLOGICAL TESTS

Figure 2:
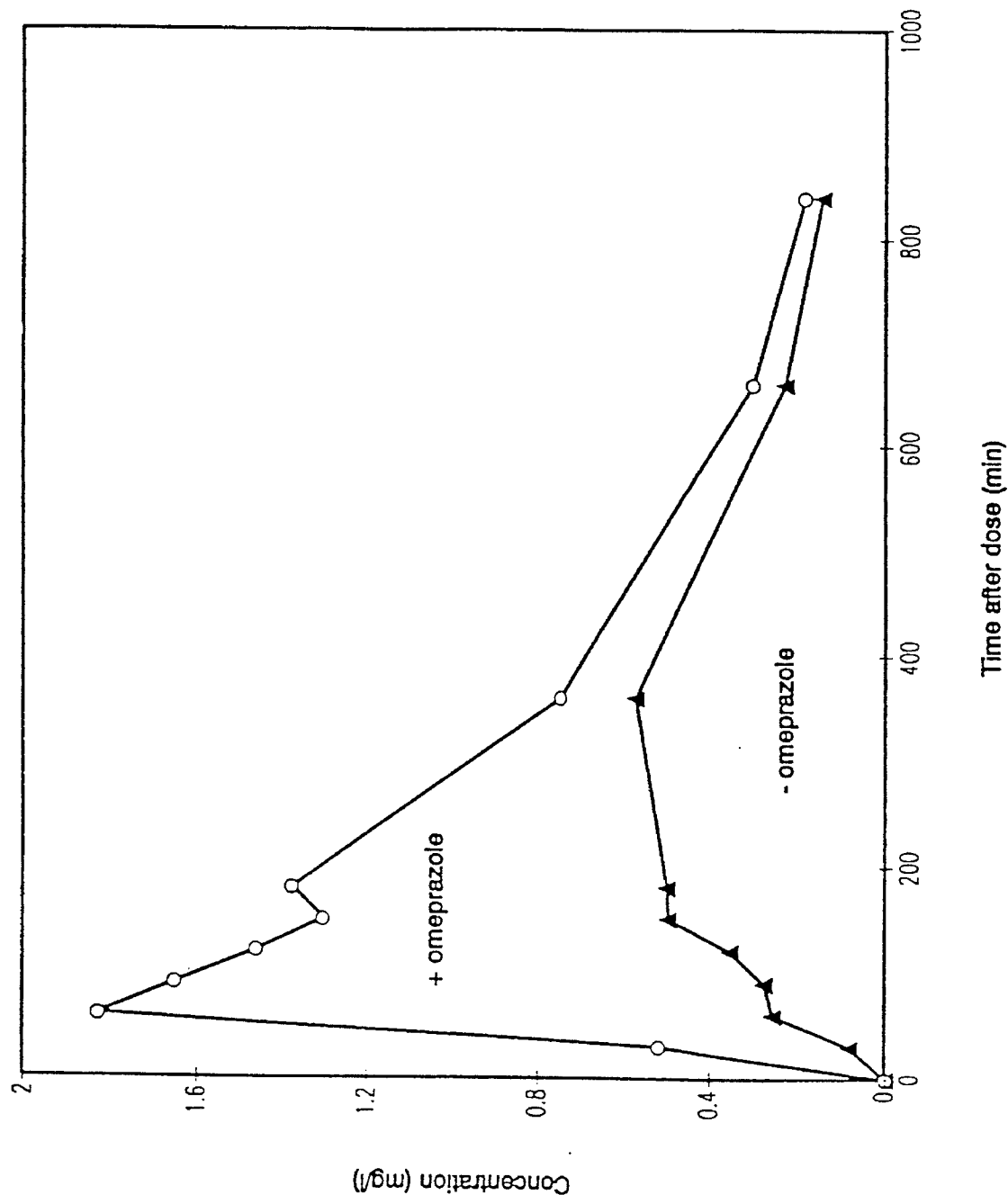
FIG. 2 represents a graph showing the blood serum levels of clarithromycin in healthy subjects during with treatment and without omeprazole.

Benzylpenicillin was administered alone to eight healthy volunteers and in combination with omeprazole and the plasma concentration was measured. When benzylpenicillin was administered alone the plasma concentrations which were expressed in terms of the area under the plasma concentration-time curve, AUC (mg-h/L), and the maximum concentration, $C_{max}$ (mg/L), and time, T, or maximum time, $T_{max}$ (h or min), were insufficient for a therapeutical effect (Table 1). When benzylpenicillin was combined with omeprazole therapeutical useful plasma concentrations were reached (Table 2). Similar results were obtained after oral administration of erythromycin lactobionate prior and after omeprazole induced reduction of acid secretion in man (Tables 3 and 4). Semidegradable macrolides, e.g. Ery-Max® and clarithromycin are absorbed to a certain extent (Tables 5 and 7). However, after administration of an acid secretion inhibitor, omeprazole, a marked increase of the bioavailability of the macrolides is shown as indicated by the difference in $C_{max}$ and AUC in healthy volunteers (Tables 6 and 8). Compare also FIG. 1 and FIG. 2 showing the accurate plasma concentrations of Ery-Max® and clarithromycin with and without omeprazole. The high plasma concentrations of the antibiotics after reduction of the gastric acid secretion is evidence for a great reduction of the degradation in the stomach of the antibiotics used. This results in an increased amount of the active antibiotic in the gastric lumen, thus resulting in increased local antimicrobial effect. It also leads to a larger amount of the antibiotic available for absorption, thus resulting in increased plasma and tissue levels of the antibiotic (increased bioavailability). The best mode of carrying out the invention at present is to combine omeprazole with erythromycin.

TABLE 1

Concentration in plasma of benzylpenicillin after oral administration Dose 1.0 g. (without omeprazole)

| Person number | Plasma concentration mg/L | | | | | | | | | Cmax mg/L | AUC H.mg/L |
|---|---|---|---|---|---|---|---|---|---|---|---|
| | 15' | 30' | 45' | 1 h | 1.5 h | 2 h | 3 h | 4 h | 6 h | | |
| 1 | 0.24 | 0.50 | 0.54 | 0.41 | 0.22 | 0.135 | 0.074 | <0.02 | <0.02 | 0.54 | 0.81 |
| 2 | 0.53 | 1.60 | 1.47 | 1.24 | 0.52 | 0.30 | 0.14 | 0.063 | <0.02 | 1.60 | 2.06 |
| 3 | 0.23 | 0.51 | 0.45 | 0.37 | 0.21 | 0.11 | 0.051 | 0.016 | <0.02 | 0.51 | 0.69 |
| 4 | 0.076 | 0.23 | 0.20 | 0.15 | 0.084 | 0.053 | 0.044 | 0.023 | <0.02 | 0.23 | 0.38 |
| 5 | 0.26 | 0.50 | 0.41 | 0.40 | 0.28 | 0.17 | 0.071 | 0.042 | <0.02 | 0.50 | 0.84 |
| 6 | 0.33 | 0.37 | 0.26 | 0.20 | 0.099 | 0.051 | 0.038 | <0.02 | <0.02 | 0.37 | 0.48 |
| 7 | 0.17 | 0.26 | 0.23 | 0.17 | 0.14 | 0.075 | 0.027 | <0.02 | <0.02 | 0.26 | 0.39 |
| 8 | 0.104 | 0.125 | 0.124 | 0.121 | 0.062 | 0.050 | 0.021 | <0.02 | <0.02 | 0.125 | 0.24 |
| Mean value ±S.D. | 0.24 | 0.51 | 0.46 | 0.38 | 0.20 | 0.118 | 0.058 | <0.03 | <0.02 | 0.52 0.46 | 0.74 0.58 |

Cmax: tdep = 4.163 P < 0.01
AUC: tdep = 5.553 P < 0.001

TABLE 2

Concentration in plasma of benzylpenicillin after oral administration Dose 1.0 g. (with omeprazole)

| Person number | Plasma concentration mg/L | | | | | | | | | Cmax mg/L | AUC H.mg/L |
|---|---|---|---|---|---|---|---|---|---|---|---|
| | 15' | 30' | 45' | 1 h | 1.5 h | 2 h | 3 h | 4 h | 6 h | | |
| 1 | 0.89 | 2.98 | 3.25 | 3.41 | 3.74 | 2.79 | 0.89 | 0.70 | 0.25 | 3.74 | 9.54 |
| 2 | 0.73 | 2.80 | 5.51 | 5.74 | 2.26 | 1.62 | 0.84 | 0.76 | 0.28 | 5.74 | 9.52 |
| 3 | 1.40 | 6.24 | 9.85 | 9.75 | 6.59 | 1.67 | 0.53 | 0.30 | 0.061 | 9.85 | 13.20 |
| 4 | 0.11 | 0.72 | 1.22 | 3.05 | 7.57 | 5.59 | 2.94 | 0.45 | 0.094 | 7.57 | 12.80 |
| 5 | 0.64 | 2.48 | 2.45 | 2.10 | 1.95 | 1.10 | 0.46 | 0.25 | 0.054 | 2.48 | 4.82 |
| 6 | 1.24 | 3.22 | 3.65 | 3.57 | 1.42 | 0.84 | 0.55 | 0.33 | 0.074 | 3.65 | 5.78 |
| 7 | 0.33 | 0.83 | 1.43 | 1.52 | 1.17 | 0.87 | 0.45 | 0.21 | 0.074 | 1.52 | 3.34 |
| 8 | 0.62 | 1.37 | 2.31 | 2.35 | 2.54 | 1.37 | 0.48 | 0.23 | 0.041 | 2.54 | 5.00 |
| Mean value | 0.745 | 2.58 | 3.71 | 3.94 | 3.41 | 1.98 | 0.89 | 0.40 | 0.116 | 4.64 | 8.00 |
| ±S.D. | | | | | | | | | | 2.87 | 3.79 |

Cmax: tdep = 4.163 P < 0.01
AUC: tdep = 5.553 P < 0.001

TABLE 3 1(2)

Concentration in plasma of erythromycin lactobionate after oral administration. Dose 1.0 g. Without preceding omeprazole treatment

| Subject number | Serum levels in mg/L at indicated times | | | | | | | | | |
|---|---|---|---|---|---|---|---|---|---|---|
| | 0 | 15' | 30' | 45' | 1 h | 1.5 h | 2 h | 3 h | 4 h | 6 h |
| 1 | <0.015 | 0.015 | 0.15 | 0.29 | 0.28 | 0.20 | 0.18 | 0.13 | 0.091 | 0.047 |
| 2 | <0.015 | 0.26 | 0.33 | 0.30 | 0.25 | 0.25 | 0.18 | 0.15 | 0.16 | 0.070 |
| 3 | <0.015 | 0.042 | 0.22 | 0.21 | 0.24 | 0.14 | 0.13 | 0.12 | 0.86 | 0.049 |
| 4 | <0.015 | 0.032 | 0.042 | 0.030 | 0.039 | 0.078 | 0.084 | 0.076 | 0.072 | 0.046 |
| 5 | <0.015 | 0.023 | 0.13 | 0.16 | 0.16 | 0.15 | 0.14 | 0.12 | 0.082 | 0.051 |
| 6 | <0.015 | 0.068 | 0.12 | 0.094 | 0.11 | 0.098 | 0.077 | 0.074 | 0.059 | 0.034 |
| 7 | <0.015 | 0.57 | 0.98 | 0.75 | 0.68 | 0.43 | 0.37 | 0.32 | 0.27 | 0.088 |
| 8 | <0.015 | 0.071 | 0.27 | 0.33 | 0.23 | 0.16 | 0.16 | 0.12 | 0.095 | 0.044 |
| Mean value | <0.015 | 0.135 | 0.28 | 0.27 | 0.25 | 0.18 | 0.165 | 0.14 | 0.11 | 0.054 |
| ±S.D. | | ±0.193 | ±0.30 | ±0.22 | ±0.19 | ±0.11 | ±0.092 | ±0.078 | ±0.070 | ±0.017 |

TABLE 3 2(2)

Concentration in plasma of erythromycin lactobionate after oral administration. Dose 1.0 g. With preceding omeprazole treatment

| Subject number | Serum levels in mg/L at indicated times | | | | | | | | | |
|---|---|---|---|---|---|---|---|---|---|---|
| | 0 | 15' | 30' | 45' | 1 h | 1.5 h | 2 h | 3 h | 4 h | 6 h |
| 1 | <0.015 | 2.9 | 7.5 | 7.6 | 7.2 | 4.9 | 4.0 | 3.1 | 3.5 | 1.4 |
| 2 | <0.015 | 2.3 | 6.8 | 5.7 | 4.5 | 5.3 | 3.6 | 3.3 | 3.2 | 1.4 |
| 3 | <0.015 | 2.7 | 12.7 | 10.9 | 7.8 | 6.0 | 5.3 | 4.5 | 4.0 | 2.4 |
| 4 | <0.015 | 3.2 | 6.0 | 3.3 | 2.5 | 1.9 | 2.8 | 2.4 | 2.4 | 0.82 |
| 5 | <0.015 | 0.25 | 2.8 | 6.4 | 4.8 | 3.0 | 2.5 | 2.0 | 2.8 | 1.2 |
| 6 | <0.015 | 1.5 | 4.9 | 3.4 | 2.7 | 1.6 | 1.8 | 1.6 | 2.1 | 0.89 |
| 7 | <0.015 | 6.3 | 9.8 | 9.3 | 6.2 | 5.3 | 4.6 | 4.6 | 3.9 | 1.8 |
| 8 | <0.015 | 3.8 | 12.8 | 13.0 | 11.1 | 10.7 | 7.3 | 5.6 | 4.3 | 2.2 |
| Mean value | <0.015 | 2.87 | 7.91 | 7.45 | 5.85 | 4.84 | 3.99 | 3.39 | 3.28 | 1.51 |
| ±S.D. | | ±1.77 | ±3.60 | ±3.46 | ±2.86 | ±2.89 | ±1.76 | ±1.40 | ±0.79 | ±0.58 |

TABLE 4

Kinetic data following oral administration(s) of erythromycin lactobionate to 8 healthy volunteers with and without co-administration of omeprazole. A cross over study.

| Omeprazole | $C_{max}$ mg/L mean ± SD | $T_{max}$ h median | AUC H.mg/L 0–6 H |
|---|---|---|---|
| YES | 8.38 ± 0.28 | 0.5 | 21.74 ± 8.64 |
| NO | 0.32 ± 0.28 | 0.75 | 0.83 ± 0.55 |

TABLE 5 1(2)

Blood serum levels of erythromycin Ery-Max ® following oral administration. Dose 500 mg. Without omeprazole treatment.

| Subject number | Serum levels in mg/L at indicated times (min) | | | | | | | | | |
|---|---|---|---|---|---|---|---|---|---|---|
| | 0 | 30 | 60 | 90 | 120 | 150 | 180 | 300 | 480 | 720 |
| 1 | 0.00 | 0.06 | 0.06 | 0.06 | 0.12 | 0.28 | 1.90 | 0.76 | 0.15 | 0.06 |
| 2 | 0.00 | 0.06 | 0.06 | 0.06 | 0.06 | 0.06 | 0.06 | 0.65 | 0.19 | 0.06 |
| 3 | 0.00 | 0.06 | 0.06 | 0.06 | 0.06 | 0.08 | 0.75 | 0.49 | 0.20 | 0.06 |
| 4 | 0.00 | 0.06 | 0.06 | 0.06 | 0.06 | 0.16 | 0.43 | 0.92 | 0.25 | 0.07 |
| 5 | 0.00 | 0.06 | 0.06 | 0.06 | 0.06 | 0.25 | 0.95 | 1.50 | 0.45 | 0.07 |
| 6 | 0.00 | 0.06 | 0.06 | 0.06 | 0.06 | 0.06 | 0.06 | 0.52 | 0.17 | 0.06 |
| 7 | 0.00 | 0.06 | 0.10 | 0.38 | 0.41 | 0.68 | 1.10 | 0.46 | 0.20 | 0.06 |
| 8 | 0.00 | 0.06 | 0.06 | 0.06 | 0.51 | 1.20 | 1.70 | 0.86 | 0.31 | 0.06 |
| Mean | 0.00 | 0.06 | 0.07 | 0.10 | 0.17 | 0.35 | 0.87 | 0.77 | 0.24 | 0.06 |
| Sdev | 0.00 | 0.00 | 0.01 | 0.11 | 0.18 | 0.40 | 0.69 | 0.34 | 0.10 | 0.01 |

TABLE 5 2(2)

Blood serum levels of erythromycin Ery-Max ® following oral administration. Dose 500 mg. Without preceding omeprazole treatment

| Subject number | AUC levels at indicated times (min) | | | | | | | | | | Tot AUC |
|---|---|---|---|---|---|---|---|---|---|---|---|
| | 0 | 30 | 60 | 90 | 120 | 150 | 180 | 300 | 480 | 720 | |
| 1 | 0 | 0.015 | 0.03 | 0.03 | 0.045 | 0.1 | 0.545 | 2.66 | 1.365 | 0.42 | 5.21 |
| 2 | 0 | 0.015 | 0.03 | 0.03 | 0.03 | 0.03 | 0.03 | 0.71 | 1.26 | 0.5 | 2.635 |
| 3 | 0 | 0.015 | 0.03 | 0.03 | 0.03 | 0.036 | 0.208 | 1.24 | 1.035 | 0.52 | 3.144 |
| 4 | 0 | 0.015 | 0.03 | 0.03 | 0.03 | 0.055 | 0.148 | 1.35 | 1.755 | 0.646 | 4.059 |
| 5 | 0 | 0.015 | 0.03 | 0.03 | 0.03 | 0.078 | 0.3 | 2.45 | 2.925 | 1.036 | 6.894 |
| 6 | 0 | 0.015 | 0.03 | 0.03 | 0.03 | 0.03 | 0.03 | 0.58 | 1.035 | 0.46 | 2.24 |
| 7 | 0 | 0.015 | 0.04 | 0.12 | 0.198 | 0.273 | 0.445 | 1.56 | 0.99 | 0.52 | 4.16 |
| 8 | 0 | 0.015 | 0.03 | 0.03 | 0.143 | 0.428 | 0.725 | 2.56 | 1.755 | 0.74 | 6.425 |
| Mean | 0 | 0.015 | 0.031 | 0.041 | 0.067 | 0.129 | 0.304 | 1.639 | 1.515 | 0.605 | |
| Sdev | 0 | 0.015 | 0.004 | 0.032 | 0.066 | 0.145 | 0.25 | 0.827 | 0.647 | 0.202 | |

AUC: 4.34 ± 1.7
$C_{max}$: 1.005

TABLE 6 1(2)

Blood serum levels of erythromycin Ery-Max ® following oral administration. Dose 250 mg. With preceding omeprazole treatment.

| Subject number | Serum levels in mg/L at indicated times (min) | | | | | | | | | |
|---|---|---|---|---|---|---|---|---|---|---|
| | 0 | 30 | 60 | 90 | 120 | 150 | 180 | 300 | 480 | 720 |
| 1 | 0.00 | 0.06 | 0.54 | 3.2 | 2.4 | 2.3 | 1.9 | 0.79 | 0.22 | 0.06 |
| 2 | 0.00 | 0.06 | 0.06 | 0.1 | 0.69 | 2.1 | 1.7 | 0.54 | 0.14 | 0.06 |
| 3 | 0.00 | 0.06 | 0.29 | 1.2 | 2.5 | 2.5 | 1.4 | 0.75 | 0.23 | 0.06 |
| 4 | 0.00 | 0.06 | 0.06 | 0.094 | 0.84 | 0.74 | 0.37 | 1.3 | 0.45 | 0.081 |
| 5 | 0.00 | 0.06 | 0.06 | 0.059 | 0.58 | 1.5 | 1.7 | 1.6 | 0.5 | 0.084 |
| 6 | 0.00 | 0.06 | 0.068 | 0.49 | 1.2 | 0.86 | 0.68 | 0.48 | 0.14 | 0.06 |

TABLE 6 1(2)-continued

Blood serum levels of erythromycin Ery-Max ® following oral administration.
Dose 250 mg. With preceding omeprazole treatment.

| Subject number | Serum levels in mg/L at indicated times (min) | | | | | | | | | |
|---|---|---|---|---|---|---|---|---|---|---|
| | 0 | 30 | 60 | 90 | 120 | 150 | 180 | 300 | 480 | 720 |
| 7 | 0.00 | 0.06 | 0.057 | 1.1 | 1.3 | 2 | 2.1 | 0.87 | 0.27 | 0.087 |
| 8 | 0.00 | 0.06 | 0.48 | 1.4 | 1.9 | 1.6 | 1.7 | 1 | 0.28 | 0.084 |
| Mean | 0.00 | 0.06 | 0.20 | 0.96 | 1.43 | 1.7 | 1.44 | 0.92 | 0.28 | 0.07 |
| Sdev | 0.00 | 0.00 | 0.21 | 1.06 | 0.76 | 0.65 | 0.61 | 0.38 | 0.13 | 0.01 |

TABLE 6 2(2)

Blood serum levels of erythromycin Ery-Max ® following oral administration.
Dose 250 mg. With preceding omeprazole treatment.

| Subject number | AUC levels at indicated times (min) | | | | | | | | | | |
|---|---|---|---|---|---|---|---|---|---|---|---|
| | 0 | 30 | 60 | 90 | 120 | 150 | 180 | 300 | 480 | 720 | Tot AUC |
| 1 | 0.00 | 0.015 | 0.15 | 0.935 | 1.4 | 1.175 | 1.05 | 2.69 | 1.515 | 0.56 | 9.49 |
| 2 | 0.00 | 0.015 | 0.03 | 0.04 | 0.198 | 0.698 | 0.95 | 2.24 | 1.02 | 0.4 | 5.59 |
| 3 | 0.00 | 0.015 | 0.088 | 0.373 | 0.925 | 1.25 | 0.975 | 2.15 | 1.47 | 0.58 | 7.825 |
| 4 | 0.00 | 0.015 | 0.03 | 0.039 | 0.234 | 0.395 | 0.278 | 1.67 | 2.625 | 1.062 | 6.347 |
| 5 | 0.00 | 0.015 | 0.03 | 0.03 | 0.16 | 0.52 | 0.8 | 3.3 | 3.15 | 1.168 | 9.173 |
| 6 | 0.00 | 0.015 | 0.032 | 0.14 | 0.423 | 0.515 | 0.385 | 1.16 | 0.93 | 0.4 | 3.999 |
| 7 | 0.00 | 0.015 | 0.029 | 0.289 | 0.6 | 0.825 | 1.025 | 2.97 | 1.71 | 0.714 | 8.187 |
| 8 | 0.00 | 0.015 | 0.0135 | 0.47 | 0.825 | 0.875 | 0.825 | 2.7 | 1.92 | 0.728 | 8.493 |
| Mean | 0.00 | 0.015 | 0.065 | 0.289 | 0.595 | 0.782 | 0.786 | 2.36 | 1.793 | 0.702 | |
| Sdev | 0.00 | 0.00 | 0.052 | 0.31 | 0.434 | 0.312 | 0.295 | 0.703 | 0.764 | 0.284 | |

AUC: 7.38 ± 1.9
$C_{max}$: 1.94

TABLE 7 1(2)

Blood serum levels of clarithromycin following oral administration.
Dose 250 mg. Without preceding omeprazole treatment

| Subject number | Serum levels in mg/L at indicated times (min) | | | | | | | | | |
|---|---|---|---|---|---|---|---|---|---|---|
| | 0 | 30 | 60 | 90 | 120 | 150 | 180 | 360 | 660 | 840 |
| 1 | 0.00 | 0.11 | 0.97 | 0.92 | 1.1 | 1.5 | 1.2 | 0.96 | 0.41 | 0.26 |
| 2 | 0.00 | 0.12 | 0.15 | 0.24 | 0.28 | 0.36 | 0.47 | 0.53 | 0.18 | 0.14 |
| 3 | 0.00 | 0.06 | 0.11 | 0.092 | 0.11 | 0.12 | 0.17 | 0.55 | 0.2 | 0.12 |
| 4 | 0.00 | 0.06 | 0.06 | 0.044 | 0.099 | 0.13 | 0.15 | 0.48 | 0.23 | 0.13 |
| 5 | 0.00 | 0.06 | 0.06 | 0.062 | 0.064 | 0.13 | 0.18 | 0.54 | 0.2 | 0.16 |
| 6 | 0.00 | 0.07 | 0.13 | 0.2 | 0.3 | 0.37 | 0.45 | 0.23 | 0.14 | 0.082 |
| 7 | 0.00 | 0.12 | 0.26 | 0.27 | 0.46 | 0.81 | 0.78 | 0.64 | 0.2 | 0.12 |
| 8 | 0.00 | 0.06 | 0.31 | 0.38 | 0.41 | 0.55 | 0.57 | 0.64 | 0.27 | 0.16 |
| Mean | 0.00 | 0.08 | 0.26 | 0.28 | 0.35 | 0.50 | 0.50 | 0.57 | 0.23 | 0.15 |
| Sdev | 0.00 | 0.03 | 0.30 | 0.28 | 0.34 | 0.47 | 0.36 | 0.20 | 0.08 | 0.05 |

TABLE 7 2(2)

Blood serum levels of clarithromycin following oral administration.
Dose 250 mg. Without preceding omeprazole treatment

| Subject number | AUC levels at indicated times (min) | | | | | | | | | | |
|---|---|---|---|---|---|---|---|---|---|---|---|
| | 0 | 30 | 60 | 90 | 120 | 150 | 180 | 360 | 660 | 840 | Tot AUC |
| 1 | 0.00 | 0.028 | 0.27 | 0.473 | 0.505 | 0.65 | 0.675 | 2.16 | 4.11 | 1.005 | 9.875 |
| 2 | 0.00 | 0.03 | 0.068 | 0.098 | 0.13 | 0.16 | 0.208 | 1 | 2.13 | 0.48 | 4.303 |

TABLE 7 2(2)-continued

Blood serum levels of clarithromycin following oral administration.
Dose 250 mg. Without preceding omeprazole treatment

| Subject number | AUC levels at indicated times (min) | | | | | | | | | | |
|---|---|---|---|---|---|---|---|---|---|---|---|
| | 0 | 30 | 60 | 90 | 120 | 150 | 180 | 360 | 660 | 840 | Tot AUC |
| 3 | 0.00 | 0.015 | 0.043 | 0.051 | 0.051 | 0.058 | 0.073 | 0.72 | 2.25 | 0.48 | 3.739 |
| 4 | 0.00 | 0.015 | 0.03 | 0.026 | 0.036 | 0.057 | 0.07 | 0.63 | 2.13 | 0.54 | 3.534 |
| 5 | 0.00 | 0.015 | 0.03 | 0.031 | 0.032 | 0.049 | 0.078 | 0.72 | 2.22 | 0.54 | 3.713 |
| 6 | 0.00 | 0.018 | 0.05 | 0.083 | 0.125 | 0.168 | 0.205 | 0.68 | 1.11 | 0.333 | 2.771 |
| 7 | 0.00 | 0.03 | 0.095 | 0.133 | 0.183 | 0.318 | 0.398 | 1.42 | 2.52 | 0.48 | 5.575 |
| 8 | 0.00 | 0.015 | 0.093 | 0.173 | 0.198 | 0.24 | 0.28 | 1.21 | 2.73 | 0.645 | 5.583 |
| Mean | 0.00 | 0.021 | 0.085 | 0.133 | 0.157 | 0.212 | 0.248 | 1.068 | 2.4 | 0.563 | |
| Sdev | 0.00 | 0.007 | 0.079 | 0.146 | 0.154 | 0.201 | 0.207 | 0.525 | 0.838 | 0.199 | |

AUC: 4.88 ± 2.24
$C_{max}$: 0.68

TABLE 8 1(2)

Blood serum levels of clarithromycin following oral administration.
Dose 250 mg. With preceding omeprazole treatment.

| Subject number | Serum levels in mg/L at indicated times (min) | | | | | | | | | |
|---|---|---|---|---|---|---|---|---|---|---|
| | 0 | 30 | 60 | 90 | 120 | 150 | 180 | 360 | 660 | 840 |
| 1 | 0.00 | 1.9 | 2.3 | 2.2 | 1.7 | 1.7 | 1.7 | 0.86 | 0.37 | 0.28 |
| 2 | 0.00 | 0.078 | 3 | 1.9 | 1.9 | 1.9 | 1.7 | 0.78 | 0.34 | 0.16 |
| 3 | 0.00 | 0.6 | 1.6 | 1.3 | 1.1 | 1.1 | 1.05 | 0.68 | 0.23 | 0.14 |
| 4 | 0.00 | 0.06 | 1.2 | 1.3 | 1.2 | 1.03 | 1.1 | 0.68 | 0.39 | 0.2 |
| 5 | 0.00 | 0.096 | 2.1 | 1.6 | 1.3 | 1.1 | 1.1 | 0.77 | 0.27 | 0.18 |
| 6 | 0.00 | 0.21 | 1.2 | 1.8 | 1.6 | 1 | 1.5 | 0.67 | 0.22 | 0.13 |
| 7 | 0.00 | 0.12 | 0.99 | 1.1 | 0.9 | 0.89 | 1.07 | 0.61 | 0.22 | 0.16 |
| 8 | 0.00 | 1.07 | 2.2 | 2 | 2 | 1.7 | 1.8 | 0.92 | 0.38 | 0.24 |
| Mean | 0.00 | 0.52 | 1.82 | 1.65 | 1.46 | 1.30 | 1.38 | 0.75 | 0.30 | 0.19 |
| Sdev | 0.00 | 0.66 | 0.69 | 0.39 | 0.40 | 0.39 | 0.33 | 0.11 | 0.08 | 0.05 |

TABLE 8 2(2)

Blood serum levels of clarithromycin following oral administration.
Dose 250 mg. With preceding omeprazole treatment.

| Subject number | AUC levels at indicated times (min) | | | | | | | | | | |
|---|---|---|---|---|---|---|---|---|---|---|---|
| | 0 | 30 | 60 | 90 | 120 | 150 | 180 | 360 | 660 | 840 | Tot AUC |
| 1 | 0.00 | 0.475 | 1.05 | 1.125 | 0.975 | 0.85 | 0.85 | 2.56 | 3.69 | 0.975 | 12.55 |
| 2 | 0.00 | 0.02 | 0.77 | 1.225 | 0.95 | 0.95 | 0.9 | 2.48 | 3.36 | 0.75 | 11.4 |
| 3 | 0.00 | 0.15 | 0.55 | 0.725 | 0.6 | 0.55 | 0.538 | 1.73 | 2.73 | 0.555 | 8.128 |
| 4 | 0.00 | 0.015 | 0.315 | 0.625 | 0.625 | 0.558 | 0.533 | 1.78 | 3.21 | 0.885 | 8.545 |
| 5 | 0.00 | 0.024 | 0.549 | 0.925 | 0.725 | 0.6 | 0.55 | 1.87 | 3.12 | 0.675 | 9.038 |
| 6 | 0.00 | 0.053 | 0.353 | 0.75 | 0.85 | 0.65 | 0.625 | 2.17 | 2.67 | 0.525 | 8.645 |
| 7 | 0.00 | 0.03 | 0.278 | 0.523 | 0.5 | 0.448 | 0.49 | 1.68 | 2.49 | 0.57 | 7.008 |
| 8 | 0.00 | 0.268 | 0.818 | 1.05 | 1 | 0.925 | 0.875 | 2.72 | 3.9 | 0.93 | 12.49 |
| Mean | 0.00 | 0.129 | 0.585 | 0.868 | 0.778 | 0.691 | 0.67 | 2.124 | 3.146 | 0.733 | |
| Sdev | 0.00 | 0.165 | 0.275 | 0.251 | 0.192 | 0.191 | 0.174 | 0.416 | 0.499 | 0.18 | |

AUC: 9.7 ± 2.1
$C_{max}$: 1.9

DISCUSSION

The advantage of the present combination of a compound that increases the intragastric pH, such as omeprazole and an acid degradable antibiotic, is that the bioavailability of the antibiotic will increase resulting in sufficient plasma levels for therapeutic effects. Another advantage is that there will be increased amounts of the acid degradable antibiotic in the gastric lumen.

Benzylpenicillin is interesting because it has a very narrow spectrum and therefore exerts a very limited effect on the normal intestinal flora.

By reducing the gastric acid secretion or acid neutralisation in the stomach the pH increases. Due to the less acidic miliew the orally administered acid degradable antibiotic will be less catabolized and thus locally exerting its antimicrobial effect. Another advantage is that increased amounts of the antibiotic will pass into the small intestine where it will be absorbed in biologically active form. Increasing the intragastric pH is also favourable for antibiotic efficacy as shown in vitro. If the pH of the medium where Helicobacter pylori is grown in vitro is reduced varying degrees below pH 7 the antibacterial properties rapidly decrease.

Those antibiotics which are weak bases e.g. macrolides will be excreted via the stomach wall due to its physicochemical properties in congruence with other known weak bases i.e. nicotine, aminopurine and omeprazole (Larsson et al., Scand. J. Gastroenterol., 1983, 85, 900–7). Thus, the antibiotic weak base will be biologically concentrated in the stomach wall, where the bacteria (e.g. Helicobacter pylori) reside.

We claim:

1. A synergistic combination comprising from about 1–200 mg omeprazole or a pharmaceutically acceptable salt thereof and from about 250 mg to 10 mg clarithromycin for the treatment of gastritis and peptic ulcer.

2. A method of orally administering an acid degradable antibiotic so as to increase its bioavailability comprising an effective amount of the synergistic combination of claim 1 to a human.

* * * * *

UNITED STATES PATENT AND TRADEMARK OFFICE
CERTIFICATE OF CORRECTION

PATENT NO. : 5,599,794
DATED : Feb. 4, 1997
INVENTOR(S) : EEK et al

It is certified that error appears in the above-identified patent and that said letters patent is hereby corrected as shown below:

Column 14, line 10, delete "10 mg" and replace by --10 g--.

Signed and Sealed this

Third Day of June, 1997

Attest:

BRUCE LEHMAN

Attesting Officer

Commissioner of Patents and Trademarks